United States Patent [19]

Minagawa et al.

[11] 4,189,409
[45] Feb. 19, 1980

[54] PROCESS FOR PREPARING A METHYLENEBIS(2-HYDROXY-4-ALKOXYBENZOPHENONE) AND ACYLOXYMETHYL 2-OH 4-ALKOXY BENZOPHENONES

[75] Inventors: Motonobu Minagawa, Koshigaya; Naohiro Kubota, Urawa; Toshihiro Shibata, Omiya, all of Japan

[73] Assignee: Argus Chemical Corporation, Brooklyn, N.Y.

[21] Appl. No.: 924,710

[22] Filed: Jul. 14, 1978

[51] Int. Cl.$^2$ .................... C08K 5/13; C07C 45/00; C07C 69/28; C07C 69/16

[52] U.S. Cl. .................... 260/23 XA; 260/23 H; 252/404; 260/45.85 R; 260/591; 560/255

[58] Field of Search .......... 260/591, 45.95 F, 45.85 R, 260/23 H, 23 XA; 560/255; 252/404

[56] References Cited

U.S. PATENT DOCUMENTS

| | | | |
|---|---|---|---|
| 3,086,988 | 4/1963 | Gordon | 260/255 |
| 3,317,462 | 5/1967 | Goldberg et al. | 260/591 |
| 3,399,237 | 8/1968 | Dressler et al. | 260/591 |

FOREIGN PATENT DOCUMENTS

50-74579 6/1975 Japan.

OTHER PUBLICATIONS

CA-67, 1967, 32417 r.

*Primary Examiner*—Hosea E. Taylor
*Attorney, Agent, or Firm*—Otto S. Kauder

[57] ABSTRACT

A novel process is provided for preparing a methylenebis(2-hydroxy-4-alkoxybenzophenone), comprising forming a novel 2-hydroxy-4-alkoxyacyloxymethylbenzophenone by a reaction of a 2-hydroxy-4-alkoxybenzophenone with a carboxylic acid and formaldehyde, and causing the 2-hydroxy-4-alkoxyacyloxymethylbenzophenone to react with a 2-hydroxy-4-alkoxybenzophenone in the presence of an acid catalyst.

Both the acyloxymethylhydroxyalkoxybenzophenone and methylenebis(2-hydroxy-4-alkoxybenxophenone) which are prepared according to this invention are useful to prevent-degradation of organic materials, particularly as light stabilizers for synthetic resins.

19 Claims, No Drawings

PROCESS FOR PREPARING A METHYLENEBIS(2-HYDROXY-4-ALKOXYBENZOPHENONE) AND ACYLOXYMETHYL 2-OH 4-ALKOXY BENZOPHENONES

BACKGROUND OF THE INVENTION

This invention relates to 2-hydroxy-4-alkoxybenzophenone ultraviolet radiation absorbing compounds, to a process for preparing such compounds, to synthetic resins stabilized against the harmful effects of ultraviolet radiation by incorporating in such resins small quantities of such compounds, and to stabilizer compositions comprising such compounds in combination with a known polymer stabilizer.

Certain 2-hydroxy-4-alkoxybenzophenone compounds are known to be effective ultraviolet absorbers and light stabilizers, with the 2-hydroxyl group critically necessary for effectiveness. There are among a large number of classes of compounds disclosed in the patent literature as meeting the requirements for an effective ultraviolet radiation absorber. In lieu of individual references, the review by G. R. Lappin in "Encyclopedia of Polymer Science and Technology" (N. Bikales, ed. New York, John Wiley-Interscience, 1971) Vol. 14, pages 125 to 148 can be consulted.

According to Lappin's review, the 18 2-hydroxybenzophenone compounds indicated to be in commercial use as stabilizers are low to moderate molecular weight compounds having a single benzophenone unit in the molecule. Lappin refers to problems of "compatibility" of the additive stabilizer with the polymer being stabilized, including such properties as the solubility of the additive in the polymer, the rate of diffusion of the additive through the polymer, and the rate of loss of the additive from the polymer. Lappin characterizes compatibility as "a sensitive function of molecular structure and not entirely predictable". Among attempts to improve on the commercially available 2-hydroxybenzophenones, Lappin indicates that longer outdoor life of polymers might be obtained with relatively high molecular weight ultraviolet radiation absorbers and states that attempts to utilize polymeric and polymerizable absorbers for this purpose had given ambiguous results and not been commercially successful.

Subsequent attempts to overcome the inadequacies of the conventional ultraviolet absorber stabilizers include a number of disclosures of 2-hydroxybenzophenones having either a plurality of benzophenone units in the molecule or functional group substitution in addition to hydroxyl and alkoxyl. Thus Lappin in U.S. Pat. No. 3,310,525 of March 21, 1967 disclosed alpha-omega-bis(2-hydroxybenzoyl)alkane stabilizers for polyesters and poly-alpha-olefin resins, having a formula

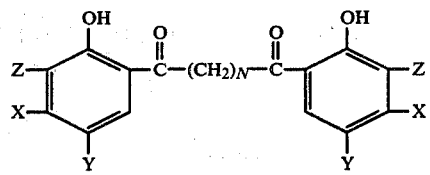

wherein n is an integer in the range from 2 to 8, and X, Y and Z are independently selected from the group of hydrogen, $C_1$-$C_4$ alkoxy and $C_1$-$C_4$ alkyl radicals.

H. Dressler in U.S. Pat. No. 3,399,237 of August 27, 1968 disclosed ultraviolet light stabilizing derivatives of 4-benzoylresorcinol having the formula

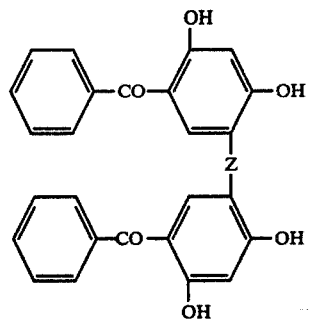

wherein Z is a member selected from the group consisting of sulfur and

and R is a member selected from the group consisting of hydrogen and alkyl having from 1–11 carbon atoms.

M. Minagawa in Japan Kokai 74 78,692 of July 29, 1974 disclosed 2-hydroxybenzophenone derivatives carrying cyclic imide substituents linked to the 4-position of the 2-hydroxybenzophenone by an alkyleneoxy group, for example 4-(2-phthalimidethoxy)-2-hydroxybenzophenone.

M. Minagawa in Japan Kokai 75 74579 of June 19, 1975 disclosed 2-hydroxybenzophenone derivatives having from 2 to 7 hydroxybenzophenone units linked through such bivalent groups as methylene, methyleneoxymethylene, cyclohexylidene, sulfide, sulfinyl, sulfonyl, alkylidene, carboxyalkylidene, and carbalkoxyalkylidene, including for example methylenebis(2-hydroxy-4-methoxybenzophenone). The location of attachment of the bivalent linking group on the 2-hydroxybenzophenone unit is nowhere specified by Minagawa.

SUMMARY OF THE INVENTION

In accordance with this invention a 2-hydroxy-4-alkoxybenzophenone having 1 to 12 carbon atoms in the alkoxy group is caused to react with formaldehyde and a carboxylic acid represented by the formula

in which R' is an alkyl group having 1 to 8 carbon atoms, preferably in the presence of a catalytically effective amount of an amino compound catalyst.

This reaction provides a novel 2-hydroxy-4-alkoxy-acyloxymethylbenzophenone represented by Formula I.

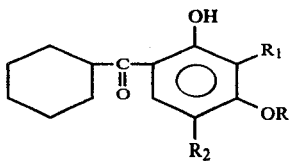

in which R is as defined above, and $R_1$ and $R_2$ are independently hydrogen or

$R'$ being hydrogen or alkyl provided that $R_1$ and $R_2$ are not simultaneously hydrogen. The new 2-hydroxy-4-alkoxy-acyloxymethylbenzophenone is an effective stabilizer for polymers such as polyamides, polyamides, polyesters both saturated and unsaturated, polyacetals, polyolefins, vinyl chloride polymers, and polyurethanes. The 2-hydroxy-4-alkoxyacyloxymethylbenzophenone can also react, in the presence of an acid catalyst, with a 2-hydroxy-4-alkoxybenzophenone to give a methylene bis(2-hydroxy-4-alkoxybenzophenone) represented by formulas II A, B, and C which is also an effective stabilizer for these polymers. When one of $R_1$ and $R_2$ is hydrogen and the other is

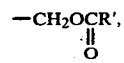

the reactions for the preparation of a new 2-hydroxy-4-alkoxy-acyloxymethylbenzophenone (reaction A) and subsequent conversion to a mixture of methylenebis(2-hydroxy-4-alkoxybenzophenone) isomers (reaction B) can be written as follows:

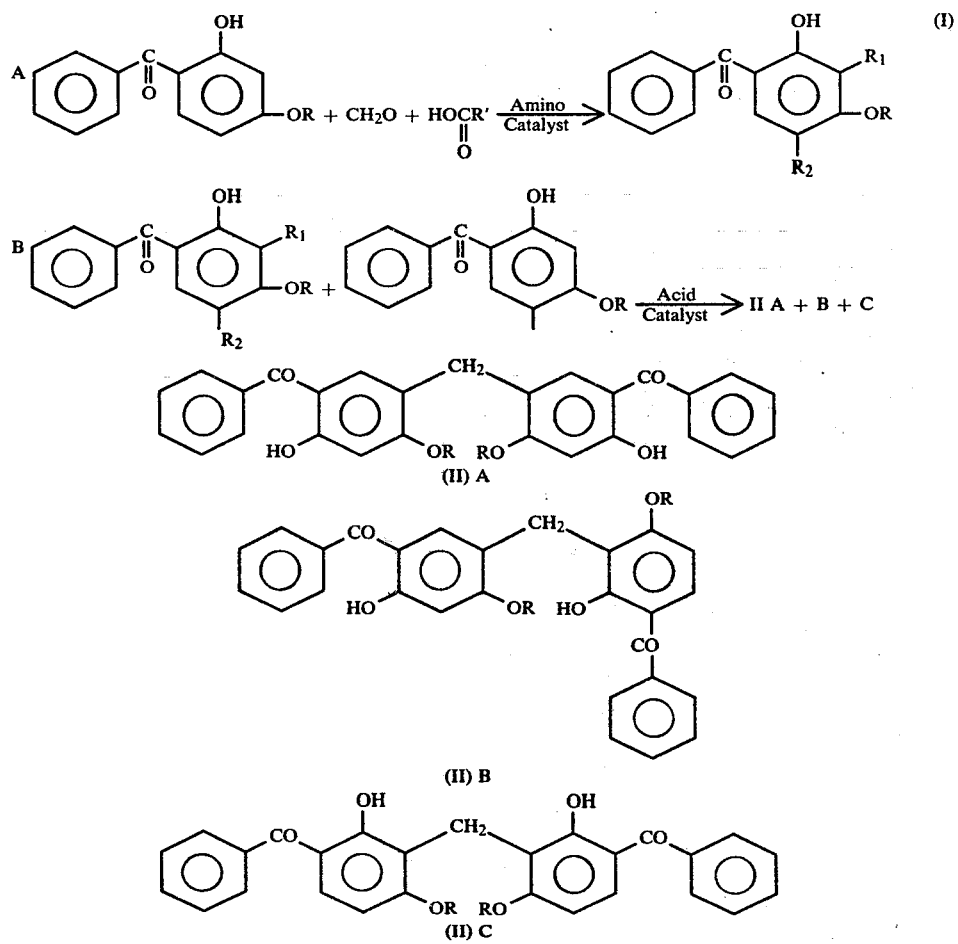

From this mixture of isomers, the 5,5'-methylenebis(2-hydroxy-4-alkoxybenzophenone) (isomer A) can usually be separated in a fairly pure condition as the least soluble isomer present. Frequently there will be no need to separate the mixture of isomers as the whole mixture as obtained the process of this invention is effective in stabilizing polymers. Moreover, mixtures of isomers A, B and C prepared according to this invention provide, particularly in polymers processed in excess of 200° C., a favorable interaction of the components resulting in better stabilization by the mixture than by any one or two of the individual components.

When in formula I both $R_1$ and $R_2$ are

the 2-hydroxy-4-alkoxybis(acyloxymethyl)-benzophenone of formula I can react with two moles of 2- hydroxy-4-alkoxybenzophenone as represented by reaction C leading to one or more of the isomeric triketones represented by formulas D, E, F, and G.

maleate polymers in styrene), cellulosic lacquers, and vinyl chloride polymer plastisols.

When the 2-hydroxy-4-alkoxybenzophenone used in

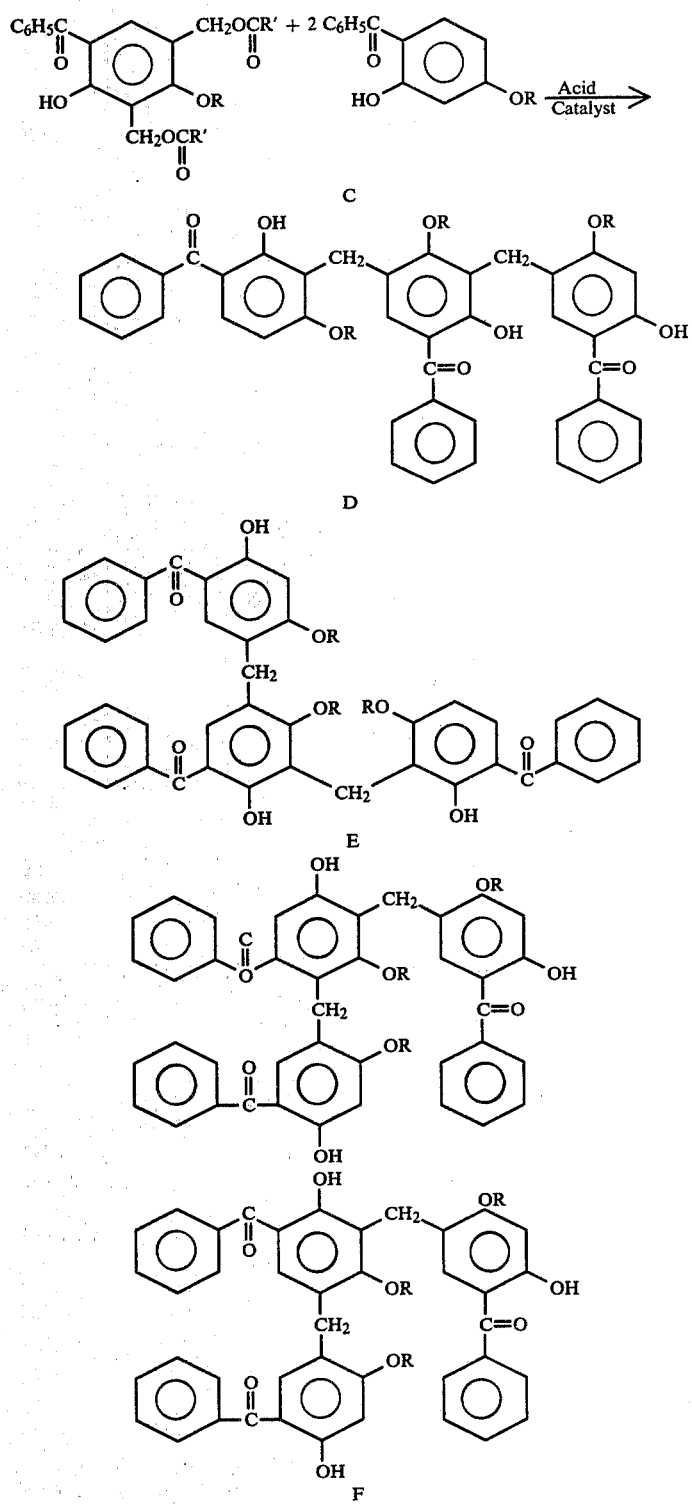

A feature of this invention is the production of liquid methylenebis(2-hydroxy-4-alkoxybenzophenone) products, usually containing several isomers, particularly useful for compounding with liquid polymer formulations such as unsaturated polyesters (solutions of glycol reaction A with carboxylic acid and formaldehyde to make the 2-hydroxy-4-alkoxy-acyloxymethylbenzophenone is different from the 2-hydroxy-4-alkoxybenzophenone used in the condensation reaction B with the 2-hydroxy-4-alkoxyacyloxymethylbenzophenone to give the methylene disubstituted benzophenone product, there can be obtained an unsymmetrical methylene-bis bis-benzophenone of formula III as well as the 3,3'-,5,3'-methylene-bis isomers thereof,

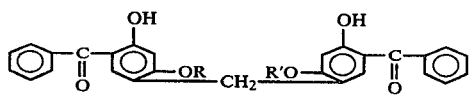 (III)

in which R and R" are dissimilar alkyl groups having 1 to 12 carbon atoms.

When a 2-hydroxy-4-alkoxy-acyloxymethylbenzophenone is used as a polymer stabilizer to protect a polymer against the harmful effects of light of wavelength less than 400 momometers, effective concentrations in the polymer range from 0.01 to 1% by weight of the polymer being stabilized. Known polymer stabilizers can be used in combination with a 2-hydroxy-4-alkoxy-acyloxymethylbenzophenone of the invention in proportions of 0.1 part of known stabilizers up to 10 parts of known stabilizer per part of 2-hydroxy-4-alkoxy-acyloxymethylbenzophenone.

DESCRIPTION OF THE PREFERRED EMBODIMENTS

In formula I of the 2-hydroxy-4-alkoxy-acyloxymethylbenzophenone of this invention, R, and R' can be for example methyl, ethyl, propyl, isopropyl, butyl, s-butyl, isobutyl, t-butyl, amyl, isoamyl, hexyl, 2-ethylbutyl, 4-methylpent-2-yl, n-heptyl, 3-heptyl, n-octyl, isooctyl, and 2-ethylhexyl. In addition R can be nonyl, decyl, n-dodecyl, etc., and R' can be hydrogen.

All forms of formaldehyde can be used in this invention, such as gaseous formaldehyde, formaldehyde in aqueous solution, paraformaldehyde, trioxane, tetraoxymethylene and other solid forms of formaldehyde. A suitable amount of formaldehyde is 1 to 1.5 moles per mole of 2-hydroxy-4-alkoxybenzophenone.

As examples of aliphatic carboxylic acid

used in this invention one may cite acetic acid, propionic acid, butyric acid, valeric acid, trimethylacetic acid, caprylic acid, 2-ethylhexoic acid, formic acid, and caproic acid. Anhydrides of these acids can also be used, for example acetic anhydride and propionic acid anhydride.

A suitable amount of aliphatic carboxylic acid is at least one mole, and preferably an excess such as 2 to 10 moles, per mole of 2-hydroxy-4-alkoxybenzophenone used.

Catalytically effective amino compounds used in this invention include ammonia, monomethylamine, monoethylamine, monopropylamine, dimethylamine, diethylamine, di-n-propylamine, diisopropylamine, di-n-butylamine, di-t-butylamine, diisobutylamine, diamylamine, ethylmethylamine, ethylisopropylamine, morpholine, pyrrolidine, and piperidine. The amount of amino compound required for catalytic effectiveness ranges from 0.01 to 0.5 mole per mole of 2-hydroxy-4-alkoxybenzophenone used. Any of the cited amino compounds can be used in the form of a salt of ammonia or amine with any of the above carboxylic acids

or in the form of reaction products with formaldehyde.

Suitable amino compound salts and formaldehyde reaction products include ammonium acetate, ammonium propionate, ethylammonium acetate, n-butylammonium 2-ethylhexoate, hexamethylenetetramine, 1,3,5-triethylhexahydrotriazine, and N-t-butylformaldimine.

The first step is carried out at a temperature with the range of 0° to 200° C., preferably 80° C. to reflux temperature (approximately 120° C.). Solvents can be used such as hydrocarbon, alcohols, ethers and amides, or an excess of the carboxylic acid reactant can serve as solvent.

The second step is carried out at a temperature within the range of −10° to 50° C., preferably 20° to 40° C. The process is preferably carried out in the presence of an organic solvent such as a hydrocarbon, an alcohol, an ether, or an amide.

As examples of solvent used in this invention, one may cite aliphatic hydrocarbons such as pentane, 2-methylbutane, hexane, 2-methylpentane, heptane and octane, aromatic hydrocarbons such as benzene, toluene, xylene, ethylbenzene, cumene, butylbenzene, cymene and diethylbenzene, alicyclic hydrocarbons such as cyclohexane, cyclopentane and ethylcyclohexane, hydrocarbon mixture such as mineral spirits, alcohols such as methanol, ethanol, isopropanol, n-butanol, isobutanol, t-butanol and pentanol, ethers such as diethylether, dipropylether, monoglyme, 2-ethoxyethanol, 2(2'-ethoxy)ethoxyethanol, anisole and butylpentylether, cyclic ethers such as dioxane, trioxane, furan, 2-methylfurane, tetrahydrofurane, tetrahydropyran and cineole, amides such as formamide, N-methylformamide, N,N-dimethylformamide, N,N-diethylformamide, acetamide and pyrrolidone, dimethylsulfoxide, etc.

In the second step, use of an acid catalyst is essential. The acid catalyst can be any acid whose 1% aqueous solution has a pH not greater than 3.

As examples of acids used in the second step, one may cite inorganic acids such as sulfuric acid, phosphoric acid, hydrochloric acid, hydrobromic acid, nitric acid and thiocyanic acid, organic acids such as paratoluenesulfonic acid, mono-, di- or trichloro-acetic acid, trifluoracetic acid, picric acid, salicylic acid, formic acid, acetic acid and propionic acid.

The order of addition of reacting materials to the mixture is not critical and can be adjusted for the sake of convenience.

New 2-hydroxy-4-alkoxy-acyloxymethylbenzophenones represented by Formula I that can be prepared in accordance with this invention include:
2-hydroxy-4-ethoxy-5-acetoxymethylbenzophenone
2-hydroxy-4-isopropoxy-3-propionyloxymethylbenzophenone
2-hydroxy-4-n-butoxy-3,5-bis(acetoxymethyl)benzophenone
2-hydroxy-4-methoxy-5-(trimethylacetoxymethyl)-benzophenone
2-hydroxy-4-n-decyloxy-3-(2-ethylhexanoyloxymethyl)benzophenone
2-hydroxy-4-n-heptoxy-5-acetoxymethylbenzophenone 2-hydroxy-4-n-dodecyloxy-3,5-bis(propionoxymethyl)benzophenone 2-hydroxy-4-isodecyloxy-3-acetoxymethylbenzophenone 2-hydroxy-4-methoxy-5-octanoyloxymethylbenzophenone 2-hydroxy-4-methoxy-3,5-bis(heptanoyloxymethyl)benzophenone Methylenebis(2-hydroxy-4-alkoxybenzophenones) represented by formulas A, B and C that can be prepared in accordance with this invention include:

3,3'-, 3,5'-, and 5,5'-methylenebis(2-hydroxy-4-methoxybenzophenone)

3,3'-, 3,5'-, and 5,5'-methylenebis(2-hydroxy-4-ethoxybenzophenone)

3,3'-, 3,5'-, and 5,5'-methylenebis(2-hydroxy-4-n-propoxybenzophenone)

3,3'-, 3,5'-, and 5,5'-methylenebis(2-hydroxy-4-isobutoxybenzophenone)

3,3'-, 3,5'-, and 5,5'-methylenebis(2-hydroxy-4-n-amyloxybenzophenone)

3,3'-, 3,5'-, and 5,5'-methylenebis(2-hydroxy-4-(2-ethylhexyloxy)benzophenone)

3,3'-, 3,5'-, and 5,5'-methylenebis(2-hydroxy-4-n-nonyloxybenzophenone)

3,3'-, 3,5'-, and 5,5'-methylenebis(2-hydroxy-4-isodecyloxybenzophenone)

3,3'-, 3,5'-, and 5,5'-methylenebis(2-hydroxy-4-n-dodecyloxybenzophenone)

The following Examples describe the preparation of particularly preferred 2-hydroxy-4-alkoxy-acyloxymethylbenzophenones represented by Formula I and -methylenebis(2-hydroxy-4-alkoxybenzophenones) represented by Formulas A, B and C.

EXAMPLE 1

Preparation of 2-hydroxy-4-methoxy-acetoxy-methylbenzophenones 22.8 g (0.1 mole) of 2-hydroxy-4-methoxy-benzophenone, 4 g of paraformaldehyde, 30 ml (0.5 mole) of acetic acid and 5.5 g (40% aqueous solution, 0.03 mole) of diethylamine was put into a flask, dissolved and heated under stirring at 100° C. for 5 hours and at reflux temperature (110° to 118° C.) for 10 hours. After cooling to room temperature, 50 ml of ether and 50 ml of water were added and carried out ether extraction.

The obtained ether phase was washed with water for two times and then treated with NaHCO$_3$ aqueous solution (10%) to remove acetic acid. A pale yellow viscous liquid was obtained by removal of water and solvent to 90° C. and 12 mm giving 27.9 g (yield 95.1%) of a mixture of 2-hydroxy-4-methoxy-5-acetoxy methylbenzophenone, 2-hydroxy-4-methoxy-3-acetoxymethylbenzophenone, and 2-hydroxy-4-methoxy-3,5-bis(acetoxymethyl)benzophenone).

EXAMPLE 2

Preparation of 2-hydroxy-4-methoxy-acetoxymethylbenzophenones with an ammonium acetate catalyst 22.8 g (0.1 mole) of 2-hydroxy-4-methoxy-benzophenone, 4.5 g of paraformaldehyde, 30 ml (0.5 mole) of acetic acid and 0.4 g (0.005 mole) of ammonium acetate was put into a flask, heated at 100° C. for five hours and at reflux temperature (110° to 118° C.) for ten hours. After cooling, ether and water was added and carried out ether extraction. The ether phase was washed with water and treated with NaHCO$_3$ aqueous solution (10%) to remove acetic acid. A pale yellow viscous liquid was obtained by stripping water and solvent to give 28.1 g (yield 93.7%) of mixed 2-hydroxy-4-methoxy-acetoxymethylbenzophenones.

EXAMPLE 3

Preparation of 2-hydroxy-4-octoxy-propiohyloxymethylbenzophenone and 5,5'-methylene-bis(2-hydroxy-4-octoxybenzophenone)

32.6 g (0.1 mole) of 2-hydroxy-4-octoxy-benzophenone, 10.6 g (37% aqueous solution) of formalin, 30 ml of propionic acid and 9.1 g (40% aqueous solution, 0.05 mole) of diethylamine was put into a flask, heated at reflux temperature for 15 hours, and unreacted propionic acid was distilled off, under vacuum.

To the crude 2-hydroxy-4-octoxy-propionyloxybenzophenone was added 50 ml of mineral spirits, 10 ml of xylene and 32.6 g of 2-hydroxy-4-octoxybenzophenone.

Ten drops of conc. H$_2$SO$_4$ was added and reacted while vigorously stirring at room temperature for 10 hours. The obtained precipitate was filtered and dissolved in hot hexane. 56.6 g (yield 85.6%) of yellow needles was obtained. The product melted at 102° to 104° C. and consisted almost entirely of 5,5'-methylenebis(2-hydroxy-4-n-octyloxybenzophenone).

EXAMPLES 4 to 12

22.8 (0.1 mole) of 2-hydroxy-4-methoxybenzophenone was heated with paraformaldehyde, diethylamine or ammonium acetate catalyst and acetic acid or acetic anhydride in quantities and conditions shown in the following Table which also reports the yield of 2-hydroxy-4-methoxyacetoxymethylbenzophenone obtained.

| Preparation Of 2-hydroxy-4-methoxy-acetoxymethylbenzophenones | | | | | | |
|---|---|---|---|---|---|---|
| Example | 2-hydroxy-4-methoxy-benzophenone | Para-formaldehyde | Diethylamine | CH$_3$COOH | Condition | Yield Based On 2-hydroxy-4-methoxy-benzophenone |
| 4 | 0.10 mole | 0.11 mole | 1.0 ml | 30 ml | 100° C. × 12hr + reflux × 12hr | 67.0% |
| 5 | 0.10 | 0.11 | 3.0 | 60 | 100° C. × 8hr + reflux × 15hr. | 58.7 |
| 6 | 0.10 | 0.11 | 5.0 | 60 | 100° C. × 5hr + reflux × 14hr. | 56.0 |
| 7 | 0.10 | 0.13 | 3.0 | 30 | 100° C. × 3hr + reflux × 17hr. | 73.3 |
| 8 | 0.10 | 0.15 | 3.0 | 30 | 100° C. × 7hr + reflux × 17hr. | 80.7 |
| 9 | 0.10 | 0.13 | 3.0 | 30 | 100° C. × 7hr + reflux × 17hr. | ca 80 |
| 10 | 0.10 | 0.13 | 3.0 | 30 | 80° C. × 7hr + reflux × 27hr. | 76.0 |
| 11 | 0.10 | 0.11 | CH$_3$COONH$_4$* 0.005 mole | 30 | 100° C. × 7hr + reflux × 18hr. | 80.4 |
| 12 | 0.10 | 0.11 | 1ml | **acetic anhydride 0.22 mole | 118° C. × 22hr + reflux × 18hr. | 81.0 |

EXAMPLES 13 to 22

Preparation of methylenebis-2-hydroxy-4-methoxybenzophenones

In each of the following examples, 2-hydroxy-4-methoxybenzophenone and one of the 2-hydroxy-4-methoxyacetoxymethylbenzophenones described above were dissolved in an organic solvent, acid catalyst was added, and reaction allowed to proceed with stirring under the indicated conditions. At the end of the reaction period the mixture was treated with water to remove the catalyst, and most of the solvent removed by vacuum distillation. Methanol (about 50 ml per mole of starting material) was added and the product allowed to crystallize. A crop of light yellow 5,5'-methylenebis-2-hydroxy-4-methoxybenzophenone, melting point 231°–232° C. was obtained by filtration. The mother liquors on evaporation gave a mixture of isomeric methylenebis(2-hydroxy-4-methoxybenzophenones) with some higher condensation products of the type represented by formulas D to G above. Details are tabulated, that also are useful ultraviolet stabilizers.

| Example | Acetoxymethyl Ester Of Example | 2-hydroxy-4-methoxy-benzophenone | Solvent | $H_2SO_4$ | Condition | 5,5' Isomer Yield Based On The Ester |
|---|---|---|---|---|---|---|
| 13 | 4, 1 mole | 1.0 mol | Ethylene Dichloride 50 ml | 1.0 mol | 40°–33° C. × 3 hr. | 24.7% |
| 14 | 6, 1 mole | 1.0 mol | Chloroform 50 ml. | 1.0 mol | 9°–28° C. × 3 hr. | 29.7 |
| 15 | 7, 1 mole | 1.0 mol | Dioxane 100 ml. | 1.0 mol | 24°–33° C. × 4.5 hr. | 28.0 |
| 16 | 8, 1 mole | 0.96 | Methylene Chloride 50 ml. | 0.1 | 21°–29° C. × 4 hr. | 17.0 |
| 17 | 9, 1 mole | 1.0 | n-Butanol 50 ml | 1.0 | reflux × 5 hr. | 16.8 |
| 18 | 9, 1 mole | 1.0 | Dioxane 50 ml. | 1.0 | room temp. × 2 hr. | 20.6 |
| 19 | 10, 1 mole | 1.0 | Spirit 50 ml + Xylene 10 ml | 3 drops | reflux × 10 hr. | 19.2 |
| 20 | 10, 1 mole | 1.0 | Benzene 50 ml. | *1 drop | reflux × 6 hr. | 14.1 |
| 21 | 11, 1 mole | 1.0 | Dioxane 50 ml. | 1.0 mol | 30°–36° C. × 5 hr. | 16.8 |
| 22 | 12, 5g | 3.1g | Dioxane 15 ml. | a few drops | room temp. 34° C. × 4 hr. | 19.3 |

*para-toluenesulfonic acid instead of sulfuric acid.

Preparation of methylenebis-2-hydroxy-4-methoxybenzophenones 2-hydroxy-methoxy-acetoxymethylbenzophenone and 2-hydroxy-4-methoxybenzophenone with acid catalyst

COMPARATIVE EXAMPLE - 1

22.8 gr (0.1 mole) of 2-hydroxy-4-methoxybenzophenone, 6.1 gr (0.075 mole, 37% aqueous solution) of formalin and 0.6g of conc. $H_2SO_4$ as catalyst was put into a flask and heated under stirring at reflux temperature for 13 hours. A high viscous reaction product was obtained. After cooling to room temperature, 20 ml of methanol was added, heated to remove impurities and washed with waer. A yellow fine powder was obtained. The fine powder was recrystallized from toluene solution for three times, obtaining 4.7 g(yield:19.9%) of yellow fine powder with melting point of 202° to 209° C.

COMPARATIVE EXAMPLE - 2

22.8 gr (0.1 mole) of 2-hydroxy-4-methoxybenzophenone and 200 ml of dichloromethane as solvent was put into a flask, dissolved and then HCl gas was bubbled into the mixture under stirring at room temperature for 6 hours. After completion of the bubbling, the mixture was heated under stirring at 30° to 35° C. for 4 hours. The mixture was washed with water, solvent stripped off and 20 ml of ethanol was added, heated to remove impurities. A yellow powder was obtained by retreatment with ethanol. The powder was recrystallized from toluene solution for two times, obtaining 3.1 g (yield:13.2%) of yellow fine powder with melting point of 196° to 201° C.

It is readily seen that the use as intermediates of the 2-hydroxy-4-alkoxy-acyloxymethylbenzophenones of this invention enables the preparation of 5,5'-methylenebis(2-hydroxy-4-alkoxybenzophenones) to be carried out with improved yield and purity of product compared to the single step procedures and in addition affords useful isomeric materials. Synthetic resins that can be stabilized with compositions comprising a 2-hydroxy-4-alkoxy-acyloxymethylbenzophenone and a known polymer stabilizer according to this invention include alphaolefin polymers such as polyethylene, polypropylene, polybutene, poly-3-methylbutene, or copolymers thereof such as ethylene-vinylacetate copolymer, ethylenepropylene copolymer, polystyrene, polyvinylacetate, acrylic ester resins, copolymers from styrene and another monomer (for example, maleic anhydride, butadiene, acrylonitrile and so on), acrylonitrile-butadiene-styrene copolymer, acrylic acid ester-butadiene-styrene copolymer, methacrylic acid ester-butadiene-styrene copolymer, methacrylate ester resin such as polymethylmethacrylate, polyvinylalcohol, ethylene and butylene terephthalate polyesters, polyamide, polycarbonate, polyacetal, polyurethane, cellulosic resin, or phenolic resin, urea resin, melamine resin, epoxy resin, unsaturated polyester, silicone resin, halogen-containing resins such as polyvinyl chloride, polyvinylidene chloride, polyvinylidene fluoride and copolymers thereof, and further rubbers such as isoprene rubber chloroprene rubber, and blends of the above resins.

Stabilizer compositions comprising a 2-hydroxy-4-alkoxy-acyloxymethylbenzophenone and a known polymer stabilizer according to this invention can be formulated and marketed in liquid, solid, and paste forms. An inert solvent can be used to facilitate handling. The 2-hydroxy-4-alkoxy-acyloxymethylbenzophenone and known polymer stabilizer can also be solubilized in one another by heating, such as at 70°–160° C. up to 4 hours, and then allowing the resulting melt to cool and harden sufficiently to be flaked and ground.

Known polymer stabilizers can be used in synthetic resin compositions together with the stabilizer compositions of this invention and can be admixed with the latter. Such known stabilizers include phenols, thiodipropionic acid esters, polyvalent metal salts of carboxylic acids, organic phosphites, 1,2-epoxides, quinones, and quaternary ammonium halides.

As examples of the phenols suited for use in this invention, one may cite the following: 2,6-di-tertiarybutyl-p-cresol, stearyl-(3,5-di-methyl-4-hydroxybenzyl)-thioglycolate, stearyl-beta(4-hydroxy-3,5-di-tertiary butylphenyl) propionate, distearyl-(4-hydroxy-3-methyl-5-tertiary butyl) benzylmalonate, 2,2'-methylenebis(4-methyl-t-tertiary butylphenol), 4,4'-methylenebis(2,6-di-tertiary butylphenol), 2,2'-methylene bis(6-(1-methylcyclohexyl)-p-cresol), bis (3,3-bis(4-hydroxy-3-tertiary butylphenyl) butyric acid) glycol ester, 4,4'-butylidenebis(6-tertiary butyl-m-cresol), 1,1,3-tris(2-methyl-4-hydroxy-5-tertiary butylphenyl)-butane, 1,3,5-tris(3,5-di-tertiary butyl-4-hydroxybenzyl)-2,4,6-trimethylbenzene, tetrakis(methylene-3-(3,5-di-tertiary butyl-4-hydroxyphenyl) propionate)methane, 1,3,5-tris(3,5-di-tertiary butyl-4-hydroxybenzyl)isocyanurate, 1,3,5-tris (3,5-di-tertiary butyl) 4-hydroxyphenyl) propionyloxyethyl) isocyanurate, 2-octylthio-4,6-di(4-hydroxy-3,5-di-tertiary butyl) phenoxy-1,3,5-triazine, and 4,4'-thiobis(6-tertiary butyl-m-cresol).

A comprehensive disclosure of useful phenols by M. Minagawa et al in U.S. Pat. No. 3,907,517 column 17 line 64 to column 23 line 61 is here incorporated by reference. When phenols are used, the concentration per 100 parts of polyolefin resin can range from 0.01 to about 0.5 part by weight.

Representative thiodipropionic acid esters include di-n-dodecyl thiodipropionate, dihexadecyl thiodipropionate, distearyl thiodipropionate, n-octyl eicosanyl thiodipropionate and n-octadecyl cyclohexane-1,4-dimethanol thiodipropionate polyester. A comprehensive disclosure of useful thiodipropionate esters by M. Minagawa et al in U.S. Pat. No. 3,869,423, column 17 line 55 to column 19 line 54 is here incorporated by reference.

Representative polyvalent metal salts include zinc, calcium, magnesium, barium, strontium and nickel salts of monocarboxylic acids having 6 to 24 carbon atoms, for example zinc benzoate, calcium palmitate, and nickel 2-ethylbutyrate. A comprehensive disclosure of useful metal salts by M. Minagawa et al in U.S. Pat. No. 3,869,423, column 19 line 56 to column 20 line 35 is here incorporated by reference.

Representative organic phosphites include triisodecylphosphite, tris (nonylphenyl phosphite), and 4,4'-isopropylidene diphenol $C_{12}-C_{15}$ mixed alkyl phosphite. A comprehensive disclosure of useful organic phosphites by M. Minagawa et al in U.S. Pat. No. 3,849,370 Column 13 line 63 to column 16 line 48 is here incorporated by reference.

Representative 1,2-epoxides include epoxysoybean oil, epoxylinseed oil, and 2-ethylhexyl epoxystearate. A comprehensive disclosure of 1,2-epoxides by M. Minagawa et al in U.S. Pat. No. 3,869,423 column 26 line 13 to line 39 is here incorporated by reference.

Quaternary ammonium halides and quinones are used as storage preservatives in unsaturated polyester resins to prevent premature gelation. Use levels range from 25 to 2000 mg/kg of resin. Representative halides include dodecyltrimethylammonium bromide, tetraethylammonium chloride, and benzyltrimethylammonium chloride. Representative quinones include benzoquinone, methylbenzoquinone, phenyl and diphenylbenzoquinones, and 1,4-naphthoquinone. A comprehensive description of unsaturated polyester resins and the use of storage preservatives therein by B. Burford in U.S. Pat. No. 3,390,121, column 7 line 1 to column 9 line 41 is here incorporated by reference.

The preparation of the stabilized resin composition is easily accomplished by conventional procedures. A heated two roll mill, for example, is a convenient compounding tool for blending stabilizer compositions of the invention with polyolefins, vinyl chloride polymers, ABS polymers, ethylene-vinyl acetate copolymers and others.

The following Examples illustrate the use of polymer stabilizer compositions of the invention.

EXAMPLE - 23

A premix of polybutylene terephthalate, 100 parts, tris-nOnylphenyl-phosphite 0.1 part, and 2-hydroxy-4-methoxy-acetoxymethylbenzophenone 0.25 part was processed by injection molding at 270° C. to prepare dumbell specimens. Using these specimens, retention of tensile strength after 500 hours in radiation was measured.

The retention of tensile strength of this composition was greater than that of a control composition omitting the 2-hydroxy-4-methoxyacetoxymethylbenzophenone.

EXAMPLE 24

A compound of ABS resin, 100 parts, zinc stearate 0.5 part, 4,4'-thiobis(2-t-butyl-5-methylphenol) 0.2 part and propionyloxymethyl-2-hydroxy-4-methoxybenzophenone was milled and molded to obtain a sheet 3 mm thick. On portions of this sheet the tensile strength before and after irradiation for 800 hours in the weatherometer was measured.

The above composition had superior retention of tensile strength compared to control composition lacking the propionyloxymethyl-2-hydroxy-4-methoxybenzophenone of this invention.

EXAMPLE 25

An unsaturated polyester resin (propyleneglycol maleatephthalate in styrene 100 parts by weight containing as storage preservatives 50 mg/kg of 2,5-diphenyl benzoquinone, 100 mg/kg of methylhydroquinone, and 600 mg/kg of trimethylbenzylammonium chloride) t-butyl peroxybenzoate 0.6 part and 2-hydroxy-4-n-octoxy-acetoxymethylbenzophenone 0.1 part was mixed and compression molded at 90°–100° C. to give a sheet 0.5 mm thick. Portions of the sheet were exposed to the radiation of a weatherometer until yellowed to a Gardner color of 5.

The above composition outlasted a control composition made without the 2-hydroxy-4-octoxy-acetoxymethylbenzophenone.

EXAMPLES 26 and 27

A mixture of methylenebis(2-hydroxy-4-methoxybenzophenones prepared as in Examples 13–22, from which a crop of crystalline 5,5'-methylenebis-2-hydroxy-4-methoxybenzophenone had been removed was tested for its photostabilizing effect in polyvinyl chloride of the following base formulation (all parts by weight):

Geon 103 EP (vinyl chloride homopolymer) — 100
Di-2-ethylhexyl phthalate — 5
Epoxysoybean oil — 5
Barium-zinc soap stabilizer — 2
Stearic acid — 0.3

Heat stability (time to blackening) was determined by air oven aging at 190° C. Photostability was determined in a weatherometer (42° C. black panel temperature) as the time to a brown discoloration.

The results are tabulated.

| Experiment | Photostabilizer (phr) | Photostability (hours) | Heat Stability (Minutes) |
|---|---|---|---|
| Control 1 | None | 500 | 90 |
| Control 2 | 2-hydroxy-4-methoxybenzophenone (0.05) | 750 | 90 |
| Control 3 | 2-hydroxy-4-methoxybenzophenone (0.1) | 750 | 90 |
| Example 26 | mixed methylenebis(2-hydroxy-4-methoxybenzophenone) (Example 6 mother liquor product (0.05) | 1000 | 90 |
| Example 27 | mixed methylenebis(2-hydroxy-4-methoxybenzophenone) (Example 6 mother liquor product) (0.1) | More than 1600 | 90 |

The results illustrate the dramatically superior photostabilizing effect of a methylenebis(2-hydroxy-4-alkoxybenzophenone) prepared according to this invention with no adverse effect on heat stability.

We claim:

1. A 2-hydroxy-4-alkoxyacyloxymethylbenzophenone represented by the formula:

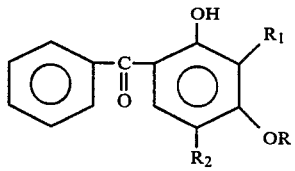

in which R is an alkyl group having 1 to 12 carbon atoms, and $R_1$ and $R_2$ are independently hydrogen atoms or saturated aliphatic acyloxymethyl groups having 2 to 9 carbon atoms, provided that $R_1$ and $R_2$ are not simultaneously hydrogen.

2. A 2-hydroxy-4-alkoxyacyloxymethylbenzophenone according to claim 1 in which R is methyl.

3. A 2-hydroxy-4-alkoxyacyloxymethylbenzophenone according to claim 1 in which R is n-octyl.

4. A 2-hydroxy-4-alkoxyacyloxymethylbenzophenone according to claim 1 in which at least one of $R_1$ and $R_2$ is acetoxymethyl.

5. A 2-hydroxy-4-alkoxy-acyloxymethylbenzophenone according to claim 1 in which at least one of $R_1$ and $R_2$ is propionoxymethyl.

6. A process for preparing a methylenebis(2-hydroxy-4-alkoxybenzophenone) represented by the formula:

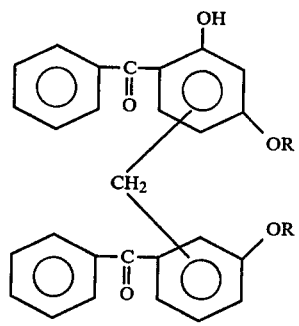

in which R is an alkyl group having 1 to 12 carbon atoms comprising the steps of treating a 2-hydroxy-4-alkoxyacyloxymethylbenzophenone of claim 1 with a 2-hydroxy-4-alkoxybenzophenone represented by the formula:

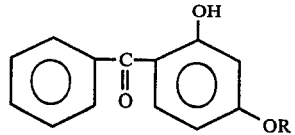

in which R is an alkyl group having 1 to 12 carbon atoms in the presence of an acid catalyst, and recovering the methylenebis(2-hydroxy-4-alkoxybenzophenone).

7. A process according to claim 6 in which the methylenebis(2-hydroxy-4-alkoxybenzophenone) is a 5,5'-methylenebis(2-hydroxy-4-alkoxymethylbenzophenone).

8. A process according to claim 6 in which the methylenebis(2-hydroxy-4-alkoxybenzophenone) is a mixture containing 5,5'-, 3,5'-, and 3,3'-methylenebis(2-hydroxyalkoxybenzophenone).

9. A stabilizer synthetic resin composition having increased resistance to deterioration on exposure to light of wavelength less than 400 nanometers, comprising a synthetic resin and 0.01 to 1% of a 2-hydroxy-4-alkoxyacyloxymethylbenzophenone according to claim 1.

10. A stabilized synthetic resin composition according to claim 9 in which the synthetic resin is vinyl chloride polymer, a styrenated polyester, or a copolymer of acrylonitrile with butadiene and sytrene.

11. A stabilizer composition capable of enhancing the resistance to deterioration on exposure of a synthetic resin to light of wavelength less than 400 nanometers comprising a 2-hydroxy-4-alkoxyacyloxymethylbenzophenone according to claim 1 and from 0.1 to 10 parts by weight per part of 2-hydroxy-4-alkoxyacyloxymethylbenzophenone of a known polymer stabilizer selected from the group consisting of phenols, quinones, quaternary ammonium, halides, polyvalent metal salts of carboxylic acids, organic phosphites, and 1,2-epoxides.

12. A stabilizer composition according to claim 11 in which the polymer stabilizer is a phenol.

13. A stabilizer composition according to claim 11 in which the polymer stabilizer is a quinone.

14. A stabilizer composition according to claim 11 in which the polymer stabilizer is a polyvalent metal salt of a monocarboxylic acid having 6 to 24 carbon atoms.

15. A stabilizer composition according to claim 11 in which the polymer stabilizer is an organic phosphite.

16. A stabilizer composition according to claim 11 in which the polymer stabilizer is a 1,2-epoxide.

17. A process according to claim 6 in which the methylenebis-2-hydroxy-4-alkoxybenzophenone) is 5,5′-methylenebis(2-hydroxy-4-methoxybenzophenone).

18. A process according to claim 6 in which the methylenebis-(2-hydroxy-4-alkoxybenzophenone) is 5,5′-methylenebis(2-hydroxy-4-n-octyloxybenzophenone).

19. A process according to claim 6 in which the methylenebis-(2-hydroxy-4-alkoxybenzophenone) is an unsymmetrical methylenebis(2-hydroxy-4-alkoxybenzophenone) with two dissimilar alkoxy groups each having one to twelve carbon atoms.

* * * * *